(12) United States Patent
Brajnovic et al.

(10) Patent No.: US 7,665,989 B2
(45) Date of Patent: Feb. 23, 2010

(54) DRILL

(75) Inventors: Izidor Brajnovic, Gothenburg (SE); Thomas Eriksson, Gothenburg (SE)

(73) Assignee: Nobel Biocare Services AG, Glattbrugg (CH)

( * ) Notice: Subject to any disclaimer, the term of this patent is extended or adjusted under 35 U.S.C. 154(b) by 573 days.

(21) Appl. No.: 11/172,292

(22) Filed: Jun. 30, 2005

(65) Prior Publication Data

US 2006/0008772 A1 Jan. 12, 2006

Related U.S. Application Data

(63) Continuation of application No. PCT/SE03/01977, filed on Dec. 19, 2003.

(30) Foreign Application Priority Data

Dec. 30, 2002 (SE) .................................. 0203900

(51) Int. Cl.
*A61C 3/02* (2006.01)

(52) U.S. Cl. ........................ 433/165; 606/79; 606/80; 606/180

(58) Field of Classification Search .................. 433/82, 433/144, 165, 166, 197–198, 224; 408/212, 408/228; 606/79–80, 180

See application file for complete search history.

(56) References Cited

U.S. PATENT DOCUMENTS

| 1,643,679 | A | * | 9/1927 | Roderick | 408/225 |
|---|---|---|---|---|---|
| 2,543,206 | A | * | 2/1951 | Smith | 408/224 |
| 2,782,824 | A | * | 2/1957 | Robinson | 408/223 |
| 2,898,787 | A | * | 8/1959 | Hofbauer | 408/230 |
| 3,346,894 | A | | 10/1967 | Lemelson | |
| 3,564,948 | A | * | 2/1971 | Pomernacki | 408/211 |

(Continued)

FOREIGN PATENT DOCUMENTS

EP    0412845 A1    2/1991

(Continued)

OTHER PUBLICATIONS

International search report for Application No. PCT/SE 2003/001977 (the PCT counterpart of the parent application).

*Primary Examiner*—Cris L Rodriguez
*Assistant Examiner*—Hao D Mai
(74) *Attorney, Agent, or Firm*—Knobbe Martens Olson & Bear LLP

(57) ABSTRACT

A drill is used on a jaw bone with overlying soft tissue and underlying, more solid bone. The drill comprises a first portion which is provided with one or more first cutting edges and with a first width or diameter. Arranged behind the first portion there is a second portion which is provided with one or more second cutting edges and with a second diameter exceeding the first width or diameter. The first portion can cooperate with soft tissues to form an initial hole, and the second portion can cooperate with the soft tissue and the more solid bone in order to enlarge said hole and create a countersunk hole in the more solid bone. The first portion is also depicted to cooperate with the more solid bone, during the second portion's formation of the countersunk hole, in order to provide a guidance hole or marker hole in the bottom of the countersink.

17 Claims, 2 Drawing Sheets

U.S. PATENT DOCUMENTS

| | | | | |
|---|---|---|---|---|
| 3,920,350 A | * | 11/1975 | Southall | 408/211 |
| 4,341,206 A | | 7/1982 | Perrett et al. | |
| 4,345,899 A | * | 8/1982 | Vlock | 433/165 |
| 4,480,952 A | * | 11/1984 | Jeremias | 408/224 |
| 4,978,350 A | * | 12/1990 | Wagenknecht | 606/312 |
| 5,007,911 A | * | 4/1991 | Baker | 606/80 |
| 5,184,689 A | * | 2/1993 | Sheirer et al. | 175/420.1 |
| 5,193,951 A | * | 3/1993 | Schimke | 408/233 |
| 5,221,166 A | * | 6/1993 | Bothum | 408/212 |
| 5,259,707 A | * | 11/1993 | Keller | 408/233 |
| 5,366,468 A | * | 11/1994 | Fucci et al. | 606/180 |
| 5,569,035 A | * | 10/1996 | Balfour et al. | 433/165 |
| 5,573,537 A | * | 11/1996 | Rogozinski | 606/80 |
| 5,593,410 A | * | 1/1997 | Vrespa | 606/312 |
| 5,697,738 A | * | 12/1997 | Stone et al. | 408/225 |
| 6,059,789 A | * | 5/2000 | Dinger et al. | 606/96 |
| 6,068,632 A | * | 5/2000 | Carchidi et al. | 606/79 |
| 6,227,774 B1 | * | 5/2001 | Haughton et al. | 408/225 |
| 6,312,432 B1 | * | 11/2001 | Leppelmeier | 606/80 |
| D455,446 S | * | 4/2002 | Collins | D15/139 |
| 6,902,400 B1 | * | 6/2005 | Roetzer | 433/165 |
| 7,140,814 B2 | * | 11/2006 | Singh et al. | 408/211 |
| 2002/0031745 A1 | * | 3/2002 | Kumar et al. | 433/165 |
| 2003/0022132 A1 | * | 1/2003 | Jesch | 433/165 |
| 2004/0081940 A1 | * | 4/2004 | Roetzer et al. | 433/165 |
| 2004/0152045 A1 | * | 8/2004 | Kachalon | 433/165 |
| 2005/0003327 A1 | * | 1/2005 | Elian et al. | 433/165 |
| 2006/0121415 A1 | * | 6/2006 | Anitua Aldecoa | 433/165 |
| 2006/0210949 A1 | * | 9/2006 | Stoop | 433/165 |
| 2009/0024129 A1 | * | 1/2009 | Gordon et al. | 606/80 |
| 2009/0116918 A1 | * | 5/2009 | Dost et al. | 408/213 |

FOREIGN PATENT DOCUMENTS

EP      424 734 A1      5/1991

* cited by examiner

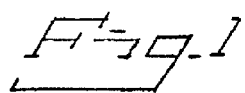
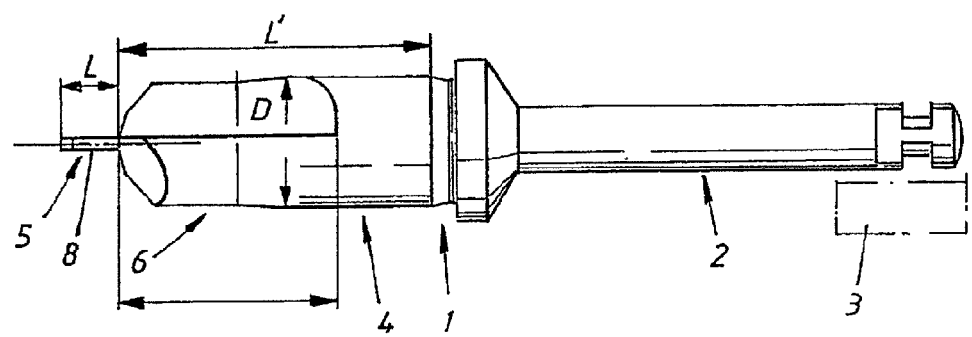
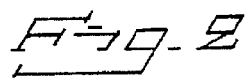
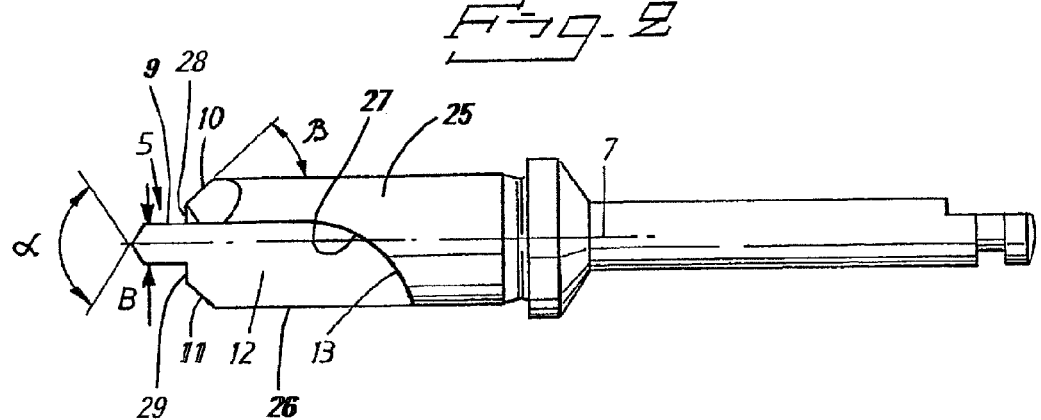
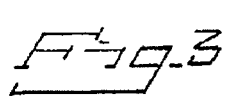
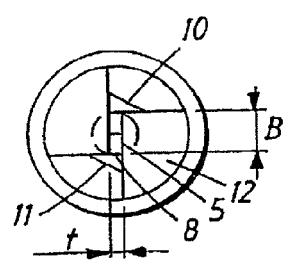

DRILL

PRIORITY INFORMATION

This application is a continuation of International Application PCT/SE2003/001977, with an international filing date of Dec. 19, 2003, which claims priority under 35 U.S.C. § 119 to Swedish Patent Application No. SE 0203900-6, filed Dec. 30, 2002, the entire contents of both of applications are expressly incorporated by reference herein.

BACKGROUND OF THE INVENTION

1. Field of the Invention

The invention also relates to a drill for use in dentistry and having said structure, and more particularly, to a drill which can be used on a jaw bone with overlying soft tissue and underlying, more solid bone.

2. Description of the Related Art

The drill is intended to be used in conjunction with the arrangement sold by Nobel Biocare AB Sweden under the name ARK (Absolute Rehabilitation Kit). Reference is made in purely general terms to the PCT applications WO 02/053055 A1, WO 02/053056 A1 and 02/053057 A1 filed by the same Applicant as for the present patent application. Reference is also made to what is generally already known in the technical field of drills.

Holes are formed in the jaw bones of patients in various circumstances and implantation situations. In cases where it is necessary to form a hole in the jaw bone, it is already known to mark out the drilling site initially and thereafter to expose the underlying jaw bone surgically and drill the hole using one or more first drills. Thereafter, a special countersinking drill is used to form a countersink intended for the head or outer part of an implant. Said drilling function has hitherto been performed using at least three different drills.

There is a need to be able to simplify and improve the hole formation function so that cutting-open of the soft tissue can be avoided and fewer drilling stages are needed, and so that the result of the hole formation is still satisfactory or can plainly be improved. It is a considerable advantage if the process of exposing the bone can be eliminated and the number of instruments and drills can be reduced without compromising the precision of the hole formation. It is also expedient if the same or similar instruments as used previously can also be used in the new context.

SUMMARY OF THE INVENTION

It is an object of the present invention is to solve at least some of the aforementioned problems. Accordingly, one aspect of the present invention comprises a drill that has a first portion designed to cooperate with the soft tissue to form an initial hole in the latter and a second portion that is designed to cooperate with the soft tissue and the more solid underlying bone for enlargement of said hole and for formation of a countersunk hole in the more solid bone. A further characteristic is that the first portion is also designed to cooperate with the more solid bone, during the second portion's formation of the countersunk hole, in order to produce a guidance hole and/or marker hole in the bottom of the countersink.

In other embodiments of the present invention, the number of first and second cutting edges can be two, three or four. The first portion can be plate-shaped and arranged in the longitudinal direction of the drill. The plate-shaped first portion can have a length of about 1.5 mm and is also designed with a tip through which the center line of the drill extends. The first portion has the first cutting edges arranged along its sides. The second cutting edges are inclined in order to form an inclined surface in the countersink. The inclination of the surface is arranged so that the surface narrows inward in a cone shape as seen in the hole formation direction. The second cutting edges can also be arranged with rectilinear parts for removing the material (gum) that arises during drilling. Further characteristics of the drill are set out in the attached dependent claims referring back to independent claim 1.

Another embodiment of the present invention comprises a drill for use in dentistry with a first portion that is arranged at the front or distal end of the drill in order to form an initial hole, and in that a second portion that is designed to enlarge said hole and form a countersunk hole. The first portion is also designed in such a way that, during the second portion's formation of the countersunk hole, it produces a guidance hole and/or marker hole in the bottom of the countersink.

Another embodiment of the present invention includes a drill that comprises a first portion which is provided with one or more first cutting edges and with a first width or diameter, and, arranged behind the first portion, a second portion which is provided with one or more second cutting edges and with a second diameter exceeding the first width or diameter.

By what has been proposed above, the problems mentioned in the introduction are solved. With the new drill, the hole formation sequence can be changed around so that, for example, in contrast to previously known techniques, the countersunk hole is formed before the hole is drilled. In connection with the formation of the countersunk hole, the bottom of the countersink is marked out, which considerably facilitates application of the drill used for the continued hole formation in the jaw bone. This has the advantage of eliminating the need for separate marking and countersinking drills, these having now been combined in one unit.

For purposes of summarizing the invention, certain aspects, advantages and novel features of the invention have been described herein. It is to be understood that not necessarily all such advantages may be achieved in accordance with any particular embodiment of the invention. Thus, the invention may be embodied or carried out in a manner that achieves or optimizes one advantage or group of advantages as taught herein without necessarily achieving other advantages as may be taught or suggested herein.

BRIEF DESCRIPTION OF THE DRAWINGS

A presently proposed embodiment of a drill according to the invention will be described below with reference to the attached drawing, in which:

FIG. 1 shows the drill in a longitudinal view.

FIG. 2 shows the drill according to FIG. 1 in a longitudinal view, but turned 90° about its longitudinal axis.

FIG. 3 is an end view of the drill according to FIG. 2, from the front.

DETAILED DESCRIPTION OF THE PREFERRED EMBODIMENT

Figure 4:
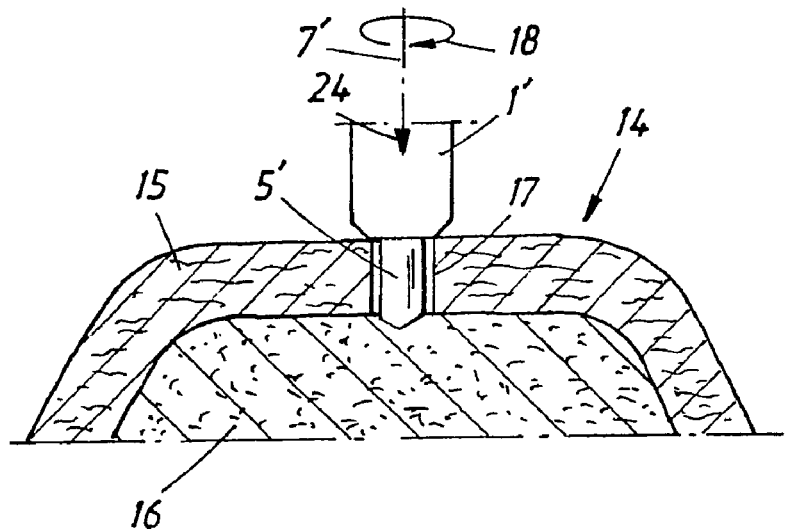
FIG. 4 is a diagrammatic longitudinal section showing a first stage of using the drill on a jaw bone which comprises a soft tissue part or gum and, located under this, more solid bone, for example cortical bone.

In FIG. 1, the drill as a whole is designated by 1. The drill comprises an attachment by which the drill is connected to a drilling machine indicated only symbolically by reference number 3. The drill also has a part 4 which bears the cutting edges in question. The part 4 comprises a first or front portion 5 and a second portion 6. In the illustrative embodiment, the front portion 5 has the shape of a plate, and in FIG. 1 the plate-shaped portion 5 is shown from the side, while FIG. 2 shows the first portion 5 in a view in which it has been turned 90° in relation to FIG. 5. The view according to FIG. 2 shows that the plate-shaped portion 5 has a tip whose angle has been indicated by α. In the illustrative embodiment, the angle is chosen at about 120°. The tip is arranged so that the center line 7 of the drill extends through the tip. The plate-shaped portion 2 is further equipped with two first cutting edges, the first cutting edge having been designated by 8 and the second cutting edge having been designated by 9. The first cutting edges 8, 9 are thus arranged on both sides of the square-shaped part of the plate-shaped portion. The portion 5 can be given an alternative design, for example the number of first cutting edges 8, 9 can be increased with further cutting edges, so that the total number of first cutting edges can be three, four, etc. It is also possible per se to use only one cutting edge although such an embodiment is not as advantageous. At its front parts, the second portion 6 is provided with cutting edges 10, 11 which are inclined in relation to the center axis 7. Said second cutting edges are situated to the side of the center line 7 and extend with angles β in relation to the center line which can be chosen at 45°. The second portion is also provided with a cylindrical surface 25 and recesses 12 via which material which arises during drilling in the jaw bone can be removed rearward and out to the side of the drill. The recesses are thus shaped with a rear curved wall 13 and first and second recess edges 26, 27. The number of second cutting edges can be varied and can, for example, be chosen as two, three, four, etc., cutting edges, such as including cutting edges 10, 11 and 28, 29. The configuration with first and second cutting edges and first and second portions can also be seen from the end view according to FIG. 3 where, inter alia, the portion 5, the cutting edge 8, the cutting edges 10 and 11, and the space 12 have been indicated. The first portion 5 is thus arranged at the front end of the drill, and the second portion 6 is arranged behind the first portion. The first portion can have a length L of about 1.5 mm. The second portion can have a length L' of about 11 mm. The plate-shaped member can be arranged with a maximum width B, see view according to FIG. 2, of the order of 1.5 mm. The second portion can be designed with a diameter of about 4.7 mm. The plate-shaped portion can have a thickness of about 0.4 mm.

Figure 5:
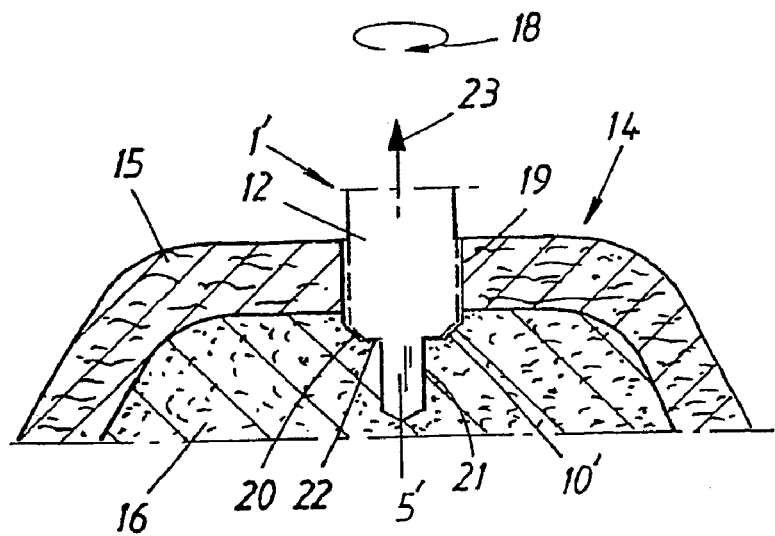
FIG. 5 shows, again in a diagrammatic longitudinal section, the use of the drill in a second stage.

FIGS. 4 and 5 show hole formation in a jaw bone 14 in two stages using the drill according to FIGS. 1, 2 and 3. The jaw bone comprises a soft tissue part or gum 15 and, located under the soft tissue, a harder and more solid bone 16, which can be cortical bone and/or trabecular bone. FIG. 4 shows the first stage in which the partially shown drill 1 is arranged with the first portion 5' penetrating through the soft tissue 5. During this penetration into and drilling of the soft tissue 15, a hole 17 is formed which, in FIG. 4, is shown slightly enlarged, for the sake of clarity, in relation to the first portion 5'. In the figure, the rotation about the center axis 7' of the drill is indicated by reference number 18. The soft tissue 15 can be drilled without having to cut open the soft tissue part at the drill site, as was previously necessary. In the case shown in FIG. 5, the drill has penetrated deeper into the gum 14. The hole 17 according to FIG. 4 has been enlarged and the enlarged hole in the soft tissue 15 has been indicated by 19. In this case too, the hole 19 has been shown enlarged in relation to the drill 1' for the sake of clarity. In addition to the enlargement of the hole 17 to give the hole 19, the drill in the stage shown in FIG. 5 has been moved down into the harder or more solid part of the jaw bone. This downward movement has meant that a counter-sunk hole 20 has been obtained in the more solid or harder bone 16. The countersink is produced using the inclined second cutting edges 10, 11 (cf. FIG. 2) on the second portion. The surface 20 in the countersink has the shape of a truncated cone and the cone angle of the surface corresponds to the one obtained with the inclined surfaces 10, 11. An inclined surface has been indicated by 10' in FIG. 5. In addition to the function of forming the countersink 20, the drill has additionally produced a guidance hole and/or marker hole 21 at the bottom 22 of the countersink. The guidance hole and/or marker hole is produced with the aid of the first portion 5' and its first cutting edges which, upon rotation 18 of the drill, drive down into the harder or solid bone at the inner and middle parts of the countersink 20 so that the hole 21 is formed. When the countersink 20 and the hole 21 have been obtained, the drill can be withdrawn in the direction of arrow 23. The direction of introduction of the drill is indicated by 24 in FIG. 4.

When the soft tissue 15 has been penetrated and the countersink 20 and the hole 21 are made, hole formation can continue using another drill (not shown in the figure) which can have a dimension corresponding to the bottom surface of the countersink. The countersink thus shaped like a truncated cone can be used for an implant (not shown) which, with its outer parts or its head, is applied in the countersink and, with its other parts, extends down into the jaw bone in the hole formed with said drill (not shown). It has been stated above that the countersink 20 has a surface shaped as a truncated cone. The countersink surface can of course have another shape, for example consisting of a cylindrical surface.

Although the foregoing systems and methods have been described in terms of certain preferred embodiments, other embodiments will be apparent to those of ordinary skill in the art from the disclosure herein. Additionally, other combinations, omissions, substitutions and modifications will be apparent to the skilled artisan in view of the disclosure herein. While certain embodiments of the inventions have been described, these embodiments have been presented by way of example only, and are not intended to limit the scope of the inventions. Indeed, the invention is not limited to the embodiment shown above by way of example, and instead it can be modified within the scope of the attached patent claims and the inventive concept.

What is claimed is:

1. A drill for use on a jaw bone with overlying soft tissue and underlying, more solid bone, comprising:
    a first portion disposed at a distal end of the drill, the first portion comprising a pair of first cutting edges, the first portion having a first width; and
    a second portion disposed at least partially intermediate the first portion and a proximal end of the drill, the second portion comprising a pair of edges extending intermediate a pair of second cutting edges and the pair of first cutting edges, the pair of second cutting edges extending at an angle relative to a longitudinal center line, the pair of edges extending from the first portion in a generally perpendicular direction relative to the longitudinal center line, the second portion having a second width that is greater than the first width, the second portion further comprising a portion having a generally cylindrical surface and at least one recess in the generally cylindrical surface thereof, the recess being formed with a wall disposed proximally relative to the pair of first cutting edges, the pair of second cutting edges, and the pair of edges of the second portion, the recess and the wall being configured to receive the soft tissue and to remove the soft tissue outwardly from the drill during drilling;

wherein the first portion is configured to cooperate with the soft tissue to form an initial hole in the soft tissue, and the second portion is configured for enlargement of said initial hole and for formation of a countersink hole in the more solid bone, and wherein the first portion is also configured to cooperate with the more solid bone, during the second portion's formation of the countersink hole, in order to produce a guidance hole or marker hole in the bottom of the countersink hole.

2. The drill as in claim 1, wherein in the drill comprises at least two first cutting edges.

3. The drill as in claim 1, wherein the first portion is formed as a plate-shaped member comprising a pair of generally parallel flat surfaces extending generally parallel to the longitudinal center line of the drill and defining a thickness therebetween and a pair of sides defining a width therebetween.

4. The drill as in claim 3, wherein the plate-shaped member has a length of about 1.5 mm and comprises a tip through which the longitudinal center line of the drill extends and wherein at least one first cuffing edge is arranged along the sides of the plate-shaped member.

5. The drill as in claim 3, wherein the sides of the plate-shaped member are parallel.

6. The drill as in claim 3, wherein the generally flat surfaces of the first portion extend co-aligned with a generally flat surface of the at least one recess in the portion having a cylindrical surface.

7. The drill as in claim 1, wherein at least one second cutting edge is inclined with respect to a longitudinal center line of the drill in order to form an inclined surface in the countersink hole that narrows inwardly as seen in a hole formation direction.

8. The drill as in claim 7, wherein at least one second cutting edge is configured with rectilinear parts for removing material that arises during drilling.

9. The drill as in claim 8, wherein at least one second cutting edge is inclined at an angle of about 45° in relation to the longitudinal centerline of the drill.

10. The drill as in claim 9, wherein the second portion has a total length of approximately 11 mm.

11. The drill as in claim 7, wherein the tip is formed by opposing first cutting edges each extending at an angle relative to the longitudinal center line of the drill.

12. The drill as in claim 11, wherein the sides of the plate-shaped member are parallel.

13. The drill as in claim 1, wherein the first width is about 1.5 mm and the second width is about 4.7 mm.

14. The drill as in claim 1, wherein the pair of second cutting edges extends at approximately a 45° angle relative to the longitudinal center line.

15. The drill as in claim 1, wherein the wall extends toward the distal end of the drill.

16. The drill as in claim 1, wherein the recess is defined by first and second recess edges, the first recess edge extending along a center axis of the drill.

17. The drill as in claim 16, wherein the second recess edge comprises a straight portion and a curved portion.

* * * * *

UNITED STATES PATENT AND TRADEMARK OFFICE
CERTIFICATE OF CORRECTION

| | | |
|---|---|---|
| PATENT NO. | : 7,665,989 B2 | Page 1 of 1 |
| APPLICATION NO. | : 11/172292 | |
| DATED | : February 23, 2010 | |
| INVENTOR(S) | : Izidor Brajnovic et al. | |

It is certified that error appears in the above-identified patent and that said Letters Patent is hereby corrected as shown below:

In Column 3, line 37, please change "cuffing" to --cutting--.

In Column 5, approximately line 13, in Claim 2, after "wherein" please delete "in".

In Column 5, line 24, in Claim 4, please change "cuffing" to --cutting--.

Signed and Sealed this

Fifth Day of October, 2010

David J. Kappos
*Director of the United States Patent and Trademark Office*